United States Patent

Kraus et al.

Patent Number: 5,454,255
Date of Patent: Oct. 3, 1995

[54] ENTRAINED AIR MEASUREMENT APPARATUS AND METHOD

[75] Inventors: Robert P. Kraus, Jr., Rochester; Stephen K. Clyde, Clifton Springs, both of N.Y.

[73] Assignee: Eastman Kodak Company, Rochester, N.Y.

[21] Appl. No.: 277,689

[22] Filed: Jul. 20, 1994

Related U.S. Application Data

[63] Continuation of Ser. No. 979,092, Nov. 19, 1992, abandoned.

[51] Int. Cl.$^6$ ............ G01N 29/00; G01N 15/06
[52] U.S. Cl. ............ 73/19.03; 73/628; 73/642
[58] Field of Search ............ 73/19.03, 628, 73/642, 600

[56] References Cited

U.S. PATENT DOCUMENTS

| | | | |
|---|---|---|---|
| 2,549,872 | 4/1951 | Willard | 171/327 |
| 2,607,858 | 8/1952 | Mason | 179/110 |
| 2,770,795 | 11/1956 | Peterson | 340/3 |
| 2,855,526 | 10/1958 | Jones | 318/8.5 |
| 3,283,562 | 8/1966 | Heisig et al. | 73/19 |
| 3,815,409 | 6/1974 | Macovski | 73/67.9 |
| 3,904,392 | 9/1975 | VanIngen et al. | 55/15 |
| 3,974,683 | 8/1976 | Martin | 73/432 PS |
| 4,070,167 | 1/1978 | Barbee et al. | 55/192 |
| 4,083,225 | 4/1978 | Day et al. | 73/19 |
| 4,097,835 | 6/1978 | Green | 340/1 R |
| 4,138,879 | 2/1979 | Liebermann | 73/19 |
| 4,205,966 | 6/1980 | Horikawa | 55/15 |
| 4,237,720 | 12/1980 | Abts | 73/19 |
| 4,445,380 | 1/1984 | Kaminski | 73/642 |
| 4,551,826 | 11/1985 | Kritz | 367/150 |
| 4,574,624 | 3/1986 | Lehtinen et al. | 73/63 |
| 4,651,555 | 3/1987 | Dam | 73/19 |
| 4,696,191 | 9/1987 | Claytor et al. | 73/600 |
| 4,763,525 | 8/1988 | Cobb | 73/599 |
| 4,821,558 | 4/1989 | Pastrone et al. | 73/19 |
| 4,911,013 | 3/1990 | Karras et al. | 73/599 |
| 5,003,516 | 3/1991 | Sato et al. | 367/150 |

*Primary Examiner*—Williams: Hezron E.
*Assistant Examiner*—J. David Wiggins
*Attorney, Agent, or Firm*—Susan L. Parulski

[57] ABSTRACT

A probe 10 and method for measuring a gaseous material, such as air, entrained in a solution (S) has a protective sheath member 14 having an ultrasonic transducer 18 encased therein and a reflecting member 42 spatially separated from the active area of face 20 of transducer 18. Upon activation of transducer 18, ultrasonic waves are emitted from transducer 18 that reflect off the gaseous material in the form of bubbles 48 and reflecting member 42 thereby producing correspondingly associated backscattered signals therefrom. Accordingly, the backscattered measurement is operative at low entrained air levels when only a few bubbles or gas 48 are present. Scattering from reflecting member 42 is useful at higher entrained air levels, approaching foam.

6 Claims, 8 Drawing Sheets

5,454,255

ENTRAINED AIR MEASUREMENT APPARATUS AND METHOD

This is a Continuation of application Ser. No. 979,092, filed 19 Nov. 1992 which application became abandoned.

FIELD OF THE INVENTION

The invention relates to an apparatus and method for measuring a gaseous material entrained in a solution, and more particularly, for measuring air entrained in a photographic coating solution.

BACKGROUND OF THE INVENTION

Air in the form of bubbles entrained in solutions, such as solutions in a photographic processing system or kettle, can result in both sensitometric and physical defects in the processed film. Bubbles are generally introduced as the contents of the kettle are being stirred but may result from other fluid dynamic steps, such as mixing in new components and liquefying solid materials. Any form of high shear mixing generally introduces bubbles as a by-product of the mixing process.

Since bubbles are generally not desirable in the final blended mixture, a number of schemes have been developed to eliminate bubbles from the solution prior to its next use in the process. There exist a number of patents that describe means for eliminating bubbles in a liquid flow, such as the apparatus disclosed in U.S. Pat. Nos. 3,904,392, 4,070,167 and 4,205,966. These patents, however, do not address the problem of detecting bubbles in the solution. Attempts to solve the problem of detecting bubbles in presumably bubble free solutions, are described, for instance, in U.S. Pat. Nos. 3,974,683, 4,138,879 and 3,283,562. The devices disclosed in these patents are designed to measure low levels of bubbles (i.e., occasional transient bubbles) in solution delivery streams and are generally not suitable for the cases of high bubbles levels normally encountered in a photographic processing chamber or kettle. There are also methods for extracting samples and measuring entrained air off-line by a Compressibility method or a density method. These methods are good for measuring high levels of entrained air, however, such techniques are inherently inadequate to solve the aforementioned problem because they are off-line and subject to the air content changing during sample handling.

SUMMARY OF THE INVENTION

It is, therefore, the object of the invention to overcome the shortcomings of the prior art. Accordingly, to solve the aforementioned problem, there is provided a probe for measuring a gaseous material in the form of bubbles entrained in a solution, the probe comprising:

a) a protective sheath member;

b) an ultrasonic transducer encased in the protective sheath member, the ultrasonic transducer having a substantially concave focusing element having an active area directed outwardly of the protective sheath member toward the solution;

c) a reflecting member spatially separated from the active area of the focusing element and cooperating therewith so that upon activation of the transducer, ultrasonic waves emitted from the active area pass through the solution, reflect off the reflecting member and gaseous material in the solution thereby producing correspondingly detectable backscattered signals associated therewith.

Moreover, a solution to the aforementioned problem is accomplished by employing the system of the invention comprising the above described probe cooperatively connected with means for digitizing the signals received from the probe, means for quantifying the digitized information and means for separating the backscattered signals produced from the reflecting member and gaseous material.

Furthermore, another solution to the above problem is achieved by employing the method of the invention using the above described probe including the steps of inserting the probe in the solution, energizing the transducer, receiving the backscattered waves from the gaseous materials and reflecting member, converting the received backscattered waves to electrical signals, separating the electrical signals, and analyzing the separated electrical signals.

BRIEF DESCRIPTION OF THE DRAWINGS

The foregoing as well as other objects, features and advantages of this invention will become more apparent from the appended Figures, wherein like reference numerals denote like elements, and wherein.

DETAILED DESCRIPTION OF THE INVENTION

Figure 1:
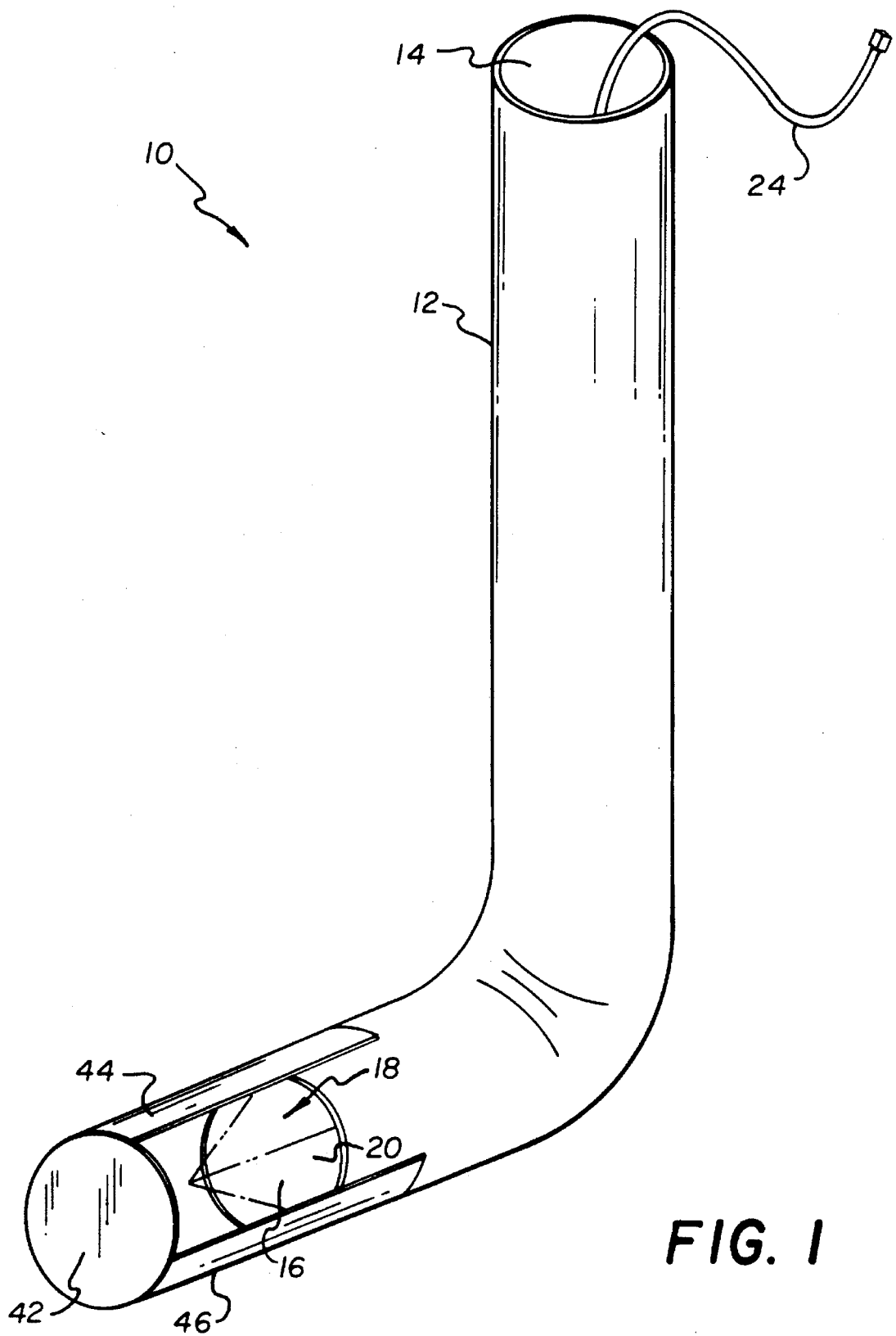
FIG. 1 is a perspective view of the probe of the invention.
Figure 2:
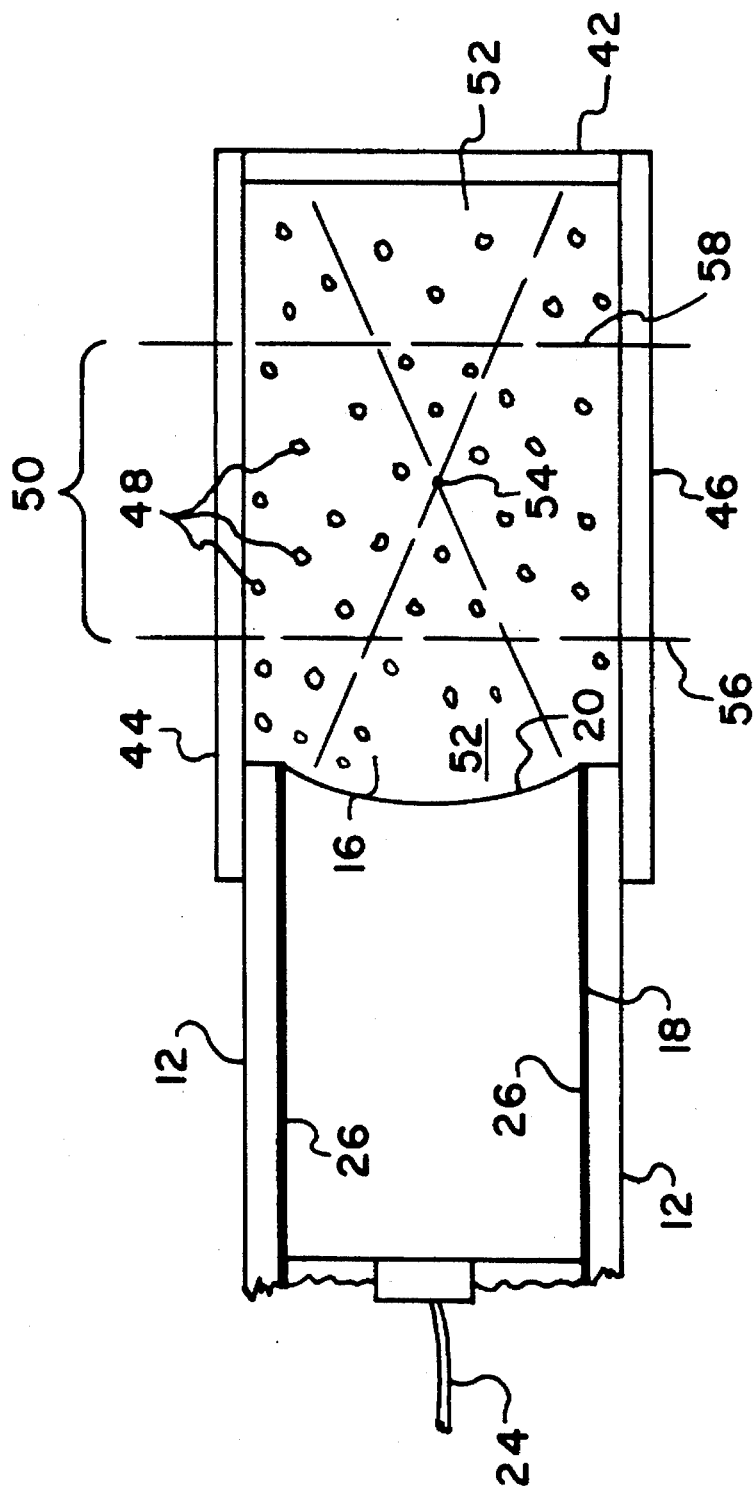
FIG. 2 is a diagrammatic view of the ultrasonic waves emitted from the active area of the transducer.

Turning now to the drawings, and more particularly to FIG. 1, there is shown probe 10 of the invention for measuring a gaseous material, such as air, entrained in a solution. Probe 10 comprises a protective sheath 12 having open ends 14, 16, preferably substantially tubular shaped stainless steel, with a focused ultrasound transducer 18 encased in end 16. Transducer 18, encased in protective sheath 12, has a substantially concaved epoxy face 20 operably connected to RF (Radio Frequency) cable 24, as best seen in FIG. 2. Transducer 18 is sealed into end 16 of protective sheath 12 with an adhesive material layer 26, preferably RTV® silicon rubber adhesive sealant manufactured by General Electric Co. This sealing technique provides a sanitary construction that is compatible with photographic fluids. Those skilled in the art will, however, appreciate that other sealing arrangements are possible within the requirements of this invention, such as an epoxy or an O-ring. Also, any number of transducers 18 could be used within the definition of the invention with similar results, although the inventors prefer either a model A302S-SU® (1 Mhz) or a model A306S-SU® (2.25 Mega hertz) both made by Panametrics located in Waltham, Mass.

Figure 3:
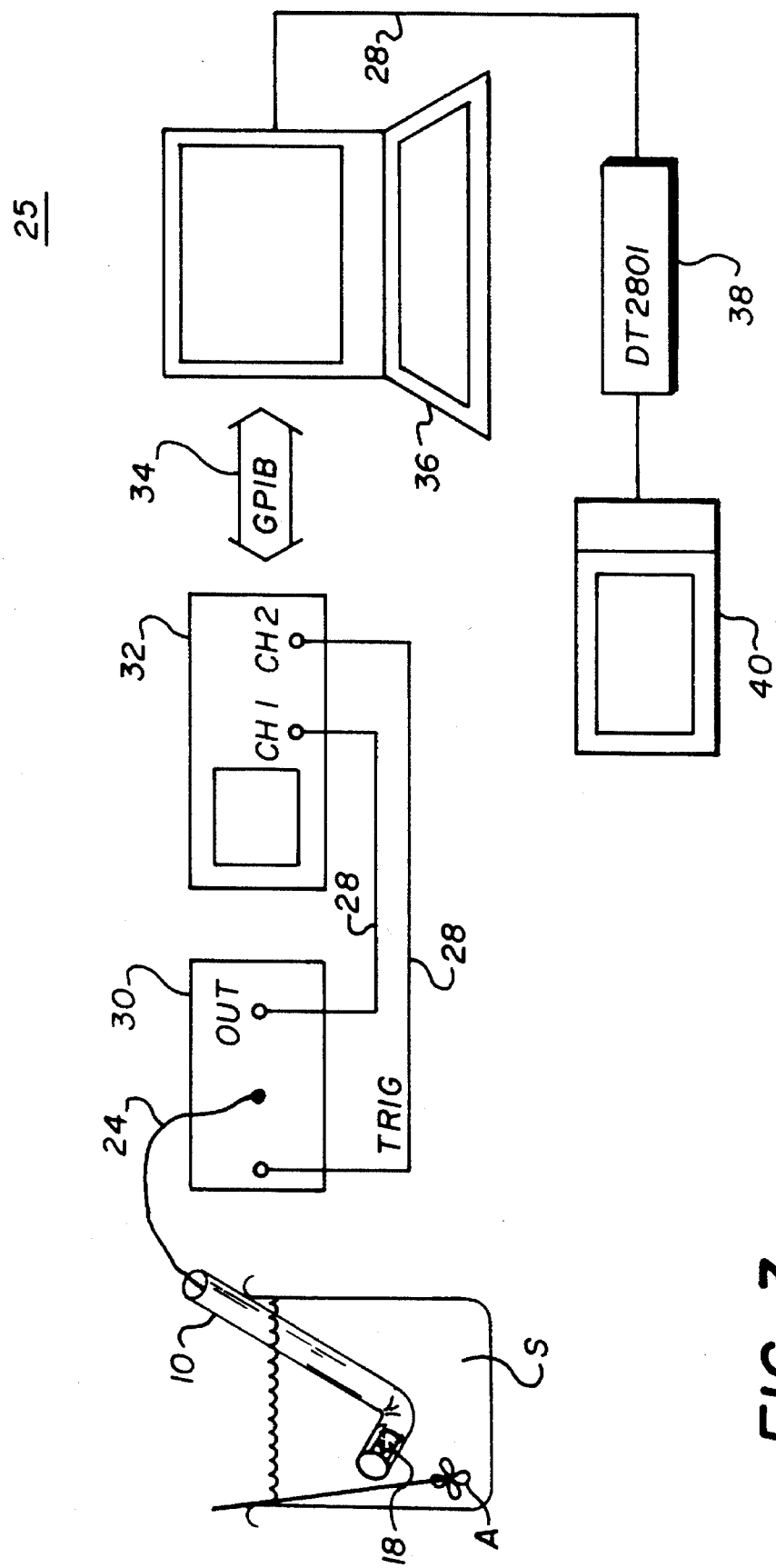
FIG. 3 is a schematic view of the entrained air measurement system of the invention.
Figure 5:
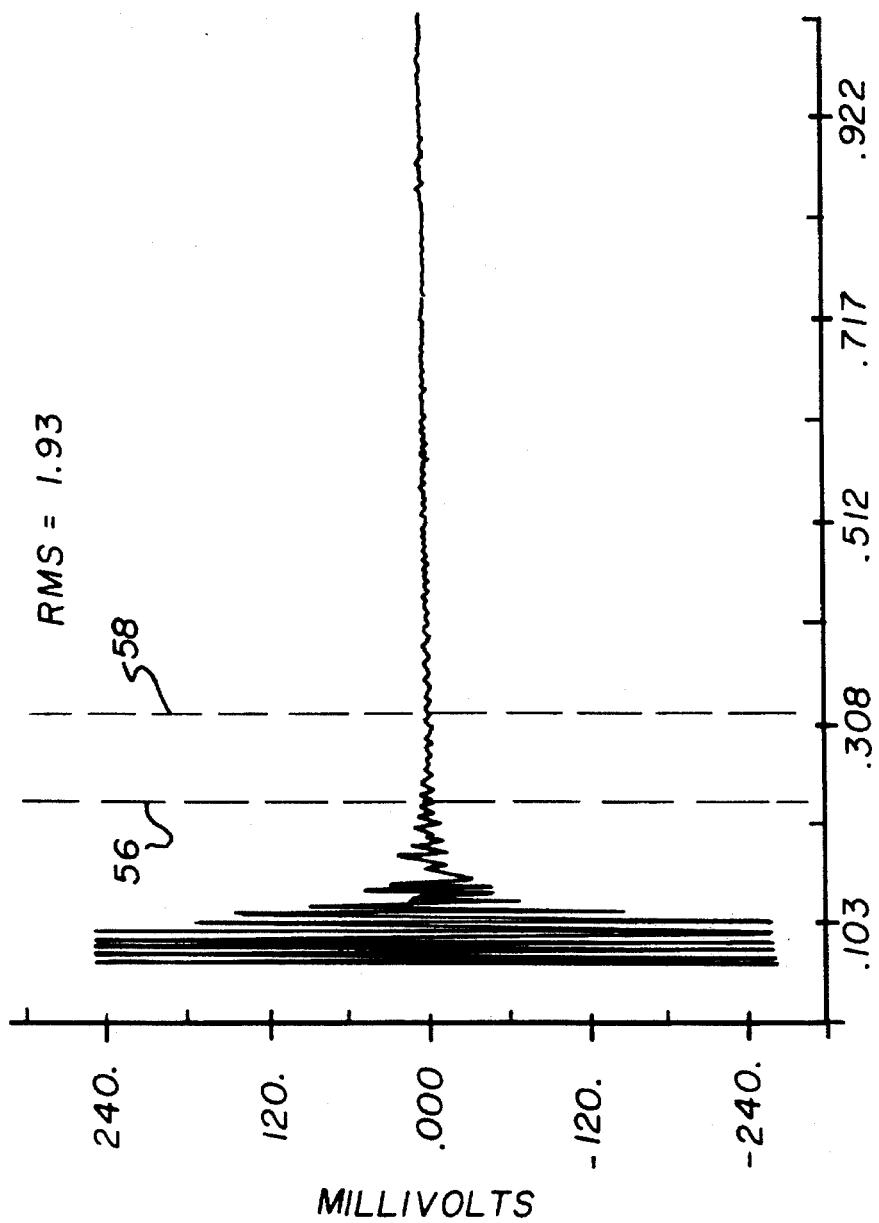
FIG. 5 is an oscilloscope trace of the received backscattered signal showing the absence of entrained bubbles.
Figure 6:
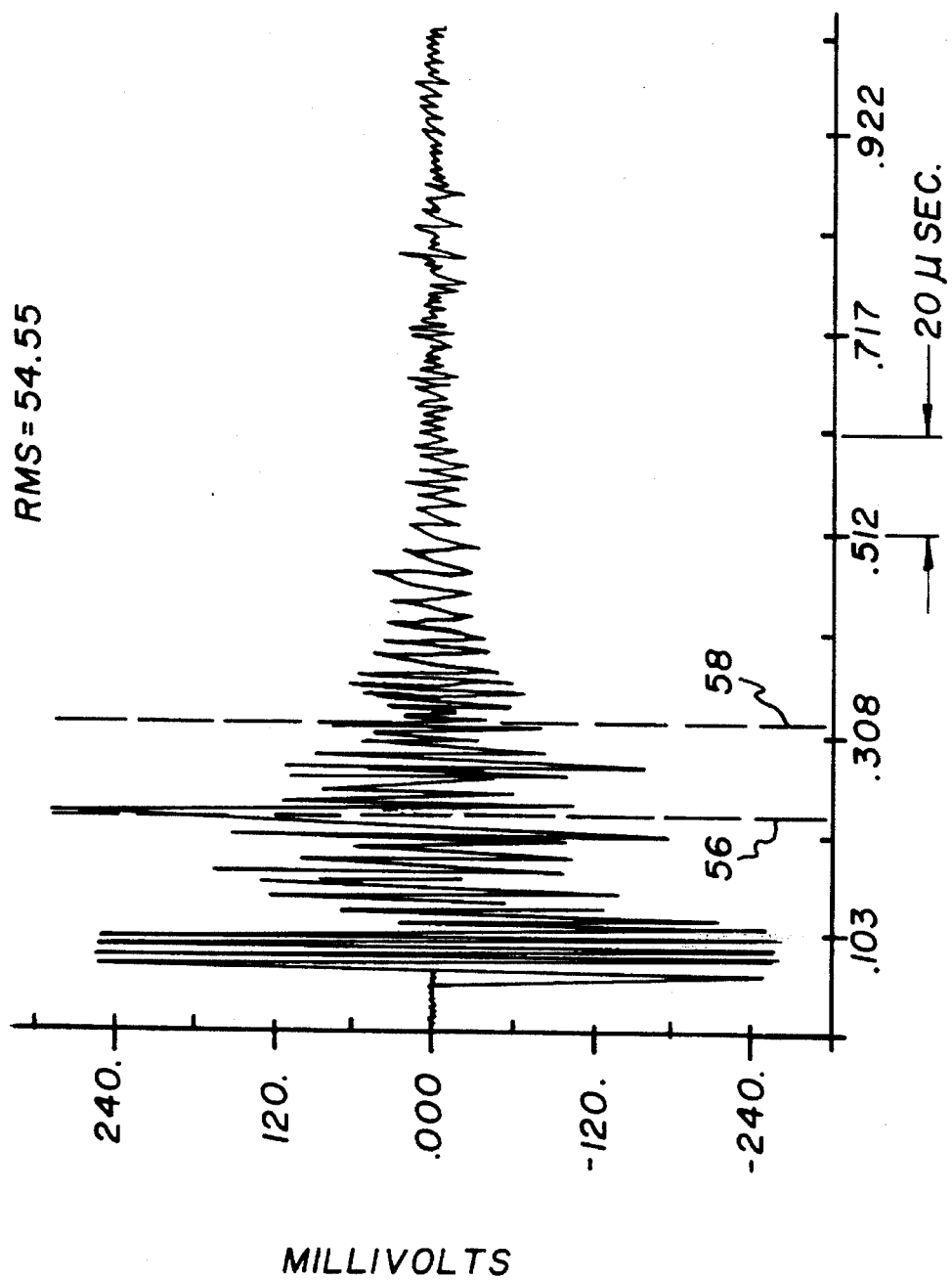
FIG. 6 is an oscilloscope trace of the received backscattered signal showing the presence of bubbles in the solution; and, FIG. 7 is an oscilloscope trace showing received backscattered signals from reflecting member with no bubbles.
Figure 7:
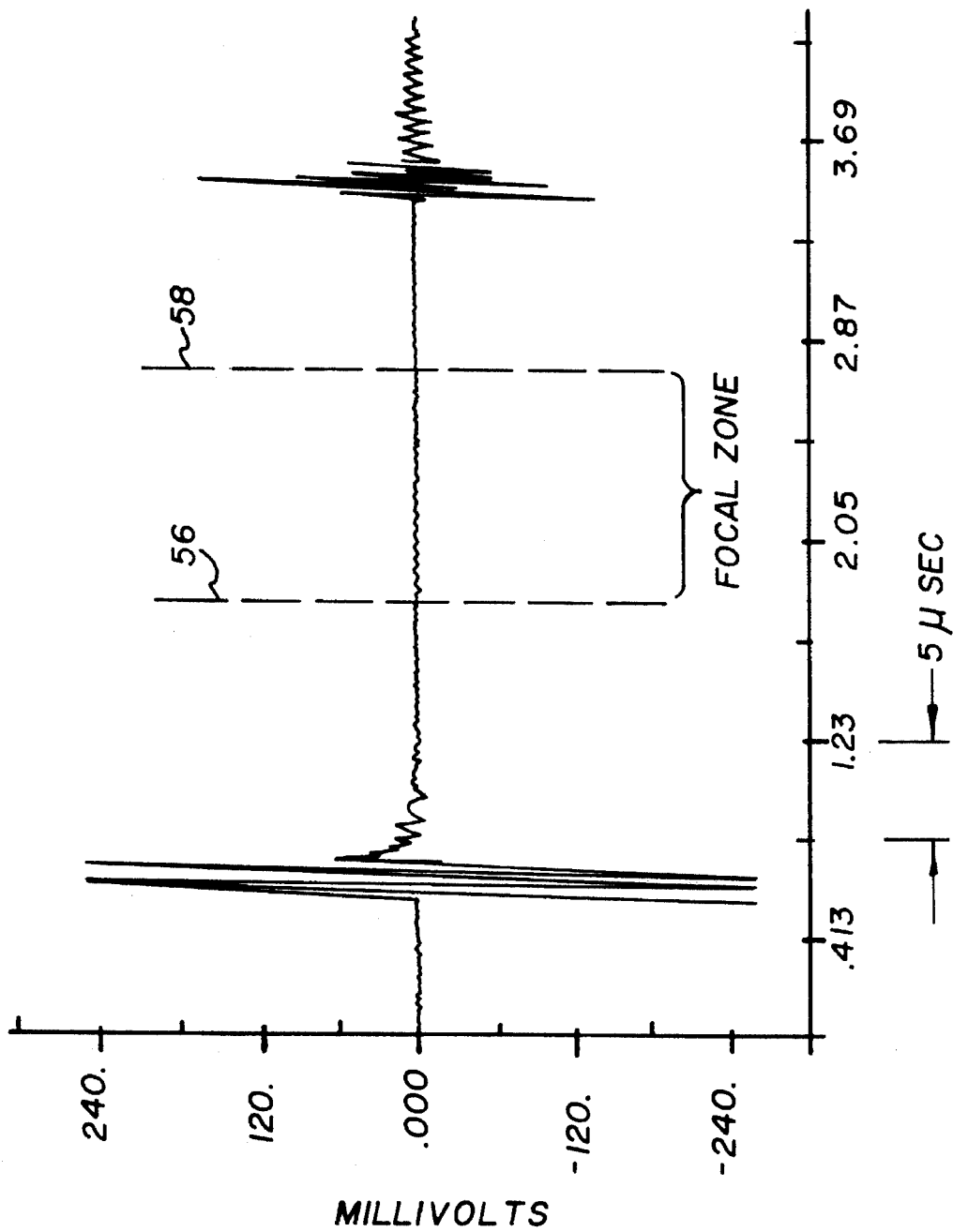

Referring to FIG. 3, the entrained air measurement system 25 of the invention is shown comprising probe 10, described above, removably positioned in a solution stream(S) or kettle being mixed by stirrer A. Probe 10 is operably connected via RF cable 24 to a commercially available ultrasonic analyzer 30 which energizes probe 10 to emit ultrasonic waves and then receives the backscattered signal for subsequent processing. One such analyzer 30 preferred by the inventors is a model 5052UA®, made by Panametrics of Waltham, Massachusetts. Analyzer 30 operates in the pulse echo mode. The output of analyzer 30 (examples of which are shown in FIGS. 5, 6, and 7) is sent to a commercially available oscilloscope 32 via RF cables 28 where it is digitized. Oscilloscope 32 preferred by the inventors is a model 2430A manufactured by Tektronix of Beaverton, Oreg. The digitized waveform is transferred over GPIB (General Purpose Interface Bus) bus 34 to information control device 36 operably connected to the probe 10 or computer for analysis. The control device 36 enables separation and qualitification of the target echo (described in detail below) and the backscattered bubble echoes; and, it processes each one independently.

Figure 4A:
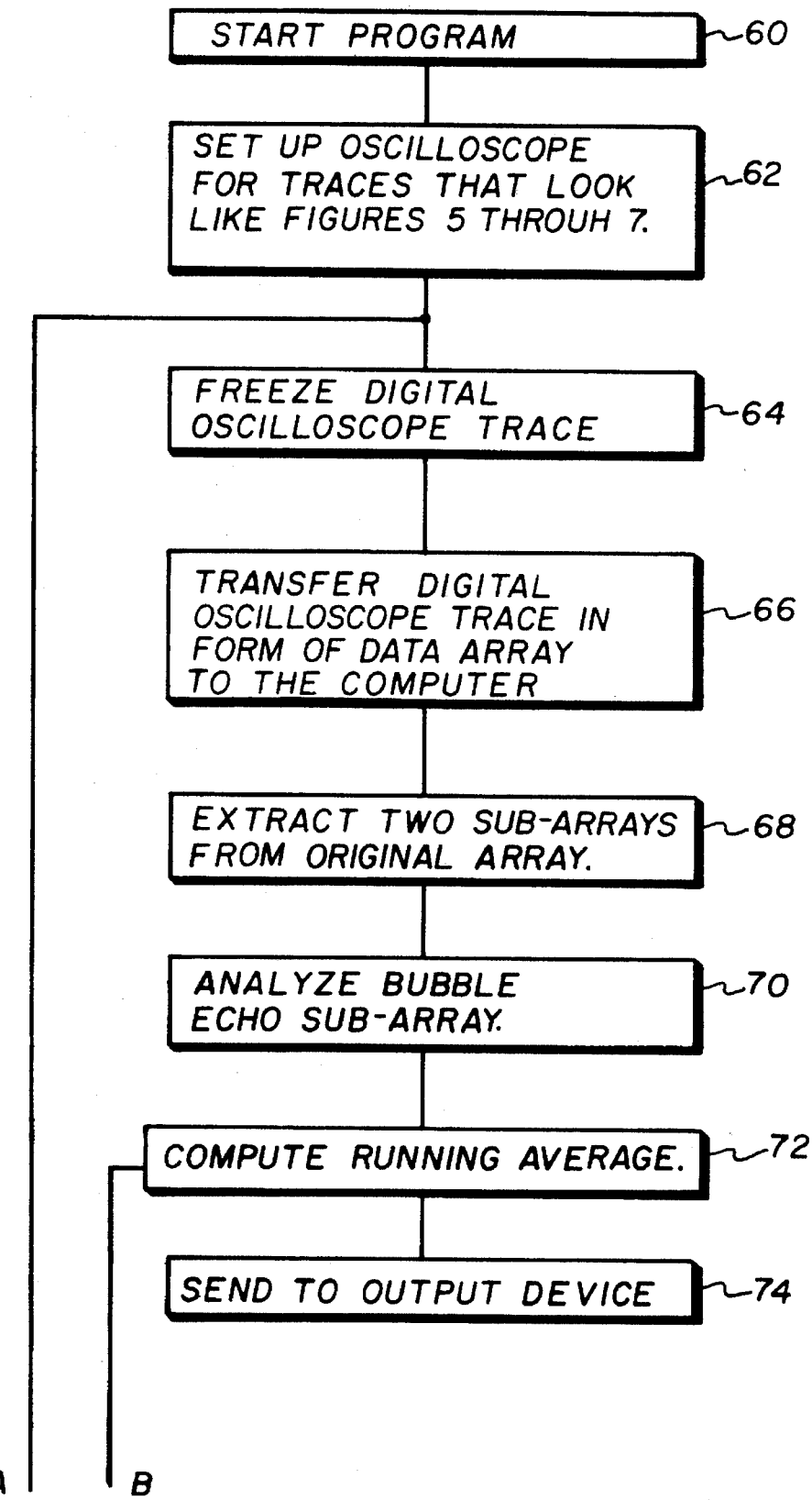
FIG. 4 is a flow chart describing the sequential operation of the control device of FIG. 3.
Figure 4B:
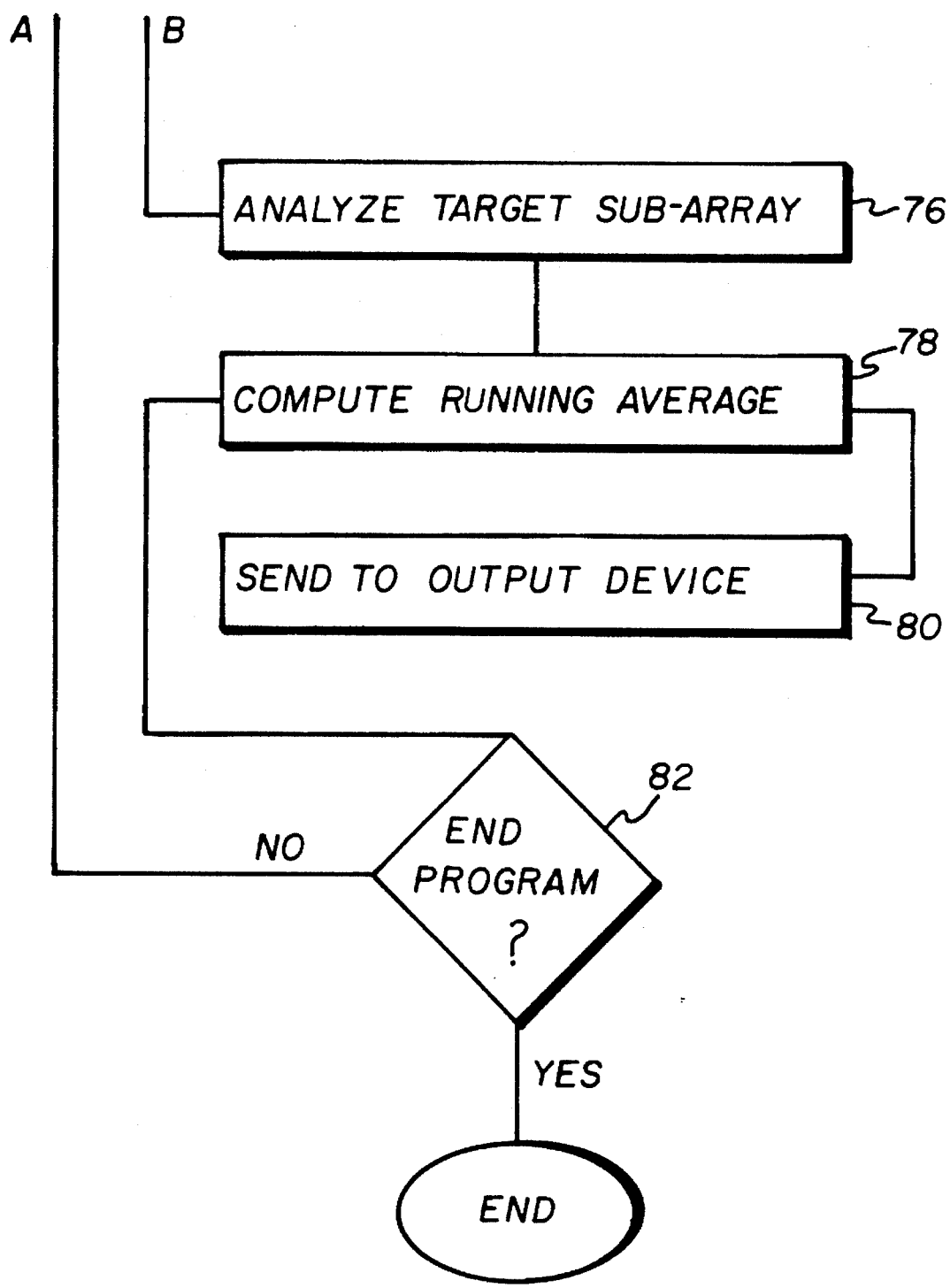

Referring now to FIG. 4, there is shown a flow chart describing the sequence for the control device 36. The first step 60 is to start the program at the beginning of the sample batch and to run for an indefinite period of time or until the measurement is complete. During this period, the control device 36 goes through a series of steps beginning with step 62. More particularly control device 36 sets up the oscilloscope 62. It then freezes the digital oscilloscope trace 64 as shown graphically in FIGS. 5–7. Then control device 36 transfers digital oscilloscope traces in the form of data arrays 66 to control device 36. This enables the data to be used for subsequent analysis. The above-mentioned steps 60–66 are available as options selected from a suitable commercial program within the definition of the invention. The commercially available program preferred by the inventors is ASYST® owned by ASYST Software Technologies Inc. of Rochester, N.Y. The array of numbers 66 can be thought of as an X-axis value (microseconds) that represents time and an associated Y-axis value (millivolts) that represents the amplitude of the echo at that time. For the analysis, this array 66 is segmented and two sub arrays are formed at step 68. One sub array consists of the X-axis values and corresponding Y-axis values for the focal zone of segment. The other sub array consists of the X-axis values and corresponding Y-axis values of the reflecting member 42 echo, shown in FIGS. 1 and 2. For reflecting member 42 echo sub array, only the maximum Y-axis value is saved for each sequentially digitized wave form 76. A running average 78 of this peak value is calculated from the sequential waveforms that result from the feedback between 82 and 64 and sent to the output device 74. For the focal zone sub array, the standard deviation of the Y-axis elements are calculated at step 70. This is equivalent to the RMS (Root Mean Squares) value with any constant DC offset removed. Therefore, the RMS value of the total backscatter echo signal is calculated. A running average 72 of this RMS value is calculated from the sequentially digitized wave forms and sent to the output device 74. In the sequence of events, a decision is made at step 82 as to whether to collect and analyze the next sequential waveform or to end the program 84. For the duration of the measurement, the preferred decision 82 is to continue the program.

ARMS value is calculated for the bubble echo signals in the focal zone and a peak amplitude is calculated for the target echo signal. In the preferred embodiment, both signals are smoothed by a running average subroutine and then converted via Digital to Analog converter 38, such as Data Translation model DT2801®, to an analog signal for output to a strip chart recorder 40 or other type of data logger. The data can also be stored in control device 36 for subsequent off-line processing.

The selection of the operating frequency and the focal length of transducer 18 (FIGS. 1 and 2) depend on the characteristics of solution (S). For silver bearing emulsions, a low frequency short focal length transducer 18 is desirable because of excessive attenuation loss caused by the silver halide grains. For non-silver bearing emulsions, a higher frequency, longer focal length transducer 18 is preferred. Reflecting member 42 (FIGS. 1 and 2) defining a target is spatially separated at end 16 from transducer 18. In one embodiment, the target or reflecting member 42 is a flat stainless steel disk that is attached to the stainless steel protective sheath 12 by two side mounts 44 and 46 and located at a distance from the end of transducer 18 further out than the focal point (FIG. 2). Side mounts 44, 46 are preferably a minimum size so as to allow for good circulation of solution (S) being measured between face 20 of transducer 18 and reflecting member 42 while at the same time being rigid enough to prevent reflecting member 42 from moving or vibrating due to the motion of solution (S) undergoing high shear mixing. Face 20 of transducer 18 should point upwardly (FIG. 3) from the horizontal in the solution stream for best results. Because face 20 of transducer 18 is concave (a requirement for focusing), bubbles may collect on face 20 if it is pointing downward. The accumulation of bubbles on face 20 of transducer 18 will prevent transmission of ultrasound in to solution (S) and effectively "blind" transducer 18.

The measurement of entrained gaseous material such as air, in solution (S) is comprised of two parts: backscatter echoes from bubbles 48 in focal zone 50 of transducer 18 and from reflecting member 42 echo (FIG. 2). The focal zone of a focused transducer is defined as the distance between the points where the on-axis signal amplitude drops to −6 decibels of the amplitude of the focal point. The location of the start of the focal zone 56 (FIGS. 2, 5, 6 and 7) and the end of the focal zone 58 (FIGS. 2, 5, 6 and 7) can be determined by standard formulas and tables such as those listed in the Technical Notes section of the *Panametrics Ultrasound Transducer Catalog*, P391, pages 30–31. These values are based on the diameter and the focal length of transducer 18 being used. For one embodiment of this invention (FIGS. 1 and 2), the diameter of transducer 18 is 0.5 inches and the focal length is 0.75 inches. From the formulas and tables, the start of the focal zone 50 begins at approximately 0.62 inches from face 20 of transducer 18 and ends at approximately 1.0 inches from face 20 of transducer 18 with the focal point at 0.75 inches from face 20 of transducer 18. In this embodiment, reflecting member 42 is located beyond the end of the focal zone 50 at approximately 1.2 inches. It should be kept in mind that the procedures listed above for calculating the location of the focal zone represent a starting point for locating the detection zone for bubbles (i.e. the detection zone and the focal zone are the same) and that this detection zone can be relocated slightly to optimize the backscatter signal from bubbles while minimizing the signal when no bubbles are present. This may be necessary to compensate for the loss properties of a particular fluid being monitored. This movement of the detection zone is done during the computer analysis of the digitized signal and does not represent a hardware change. In general the location of the detection zone is very close to focal zone 50 so we will, in general, use the term focal zone. Moreover, the relationship of ultrasonic field 52 with respect to bubbles 48 and reflecting member 42 is shown clearly in FIG. 2. In operation, ultrasonic transducer 18 is excited by an electrical impulse and an ultrasonic wave is emitted from face 20 of transducer 18 into solution (S). Because of the concave geometry of face 20 of transducer 18, the energy is concentrated at the focal point 54 of transducer 18. Ultrasound reflects from bubbles 48 within the ultrasonic field 52 and these echoes return to transducer 18. The backscatter part of the measurement is based on the total backscatter power from bubbles 48 located in focal zone 50 of transducer 18. Focal zone 50 echoes are separated from the other bubbles 48 echoes and reflecting member 42 echoes by flow chart step 68 previously described. The backscattered bubble signal is converted to an electrical signal by transducer 18 and then processed, as described in FIG. 4, to generate a RMS value of the returned signal. FIGS. 5 and 6 show oscilloscope 32 traces of the received backscattered signals. FIG. 5 manifests the absence of bubbles 48 in solution (S) and FIG. 6 shows evidence of bubbles 48. Vertical broken spaced lines 56 and 58 (FIGS. 2,5,6, & 7) represent the focal zone 50. It is the RMS value of the signal between the broken spaced lines 56,58 that is measured. The position of broken spaced lines 56,58 in FIGS. 5 and 6 represent the focal zone 50, shown in FIG. 2.

The second part of the measurement involves the amplitude of reflecting member 42 echo. FIG. 2 shows reflecting member 42 located outside of focal zone 50 of transducer 18. An echo from reflecting member 42 returns to transducer 18 at a time later than the echoes from bubbles 48 and this echo is converted by transducer 18 to an electrical signal which is separated from the signals generated by bubble 48 echoes in FIG. 4 step 68 previously described in the processing electronics. FIG. 7 shows an oscilloscope 32 trace of the received reflecting member 42 echo with no bubbles 48 present in solution (S). As before, focal zone 50 is located between broken spaced lines 56 and 58.

By using both measurement techniques, the dynamic range of the entrained air measurement is greatly increased. The backscatter measurement is operative at low entrained air levels when only a few bubbles 48 are present. Reflecting member 42 is useful at higher entrained air levels, approaching foam. The responses of the two measurements are opposite each other. For backscatter, the measurement increases from zero with increasing numbers of bubbles 48, up to a saturation limit. For the target or reflecting member 42 measurement, the signal decreases from some maximum value which depends upon the loss properties of solution (S) and the exact spacing of the reflecting member 42 from face 20 of transducer 18, to zero with increasing amounts of air.

Accordingly, an important advantageous effect of the present invention is that it provides a probe 10 and method for accurately measuring a gaseous material entrained at both high and low levels in a solution (S), such as a photographic coating solution.

The invention has therefore been described with reference to certain embodiments thereof, but it will be understood that variations and modifications can be effected within the scope of the invention.

What is claimed is:

1. A probe for measuring a gaseous material entrained in a photographic solution, said probe comprising:

a) a protective sheath member, adapted to be inserted into the solution;

b) an ultrasonic transducer oriented and encased in said protective sheath member for insertion into a photographic solution, said ultrasonic transducer adapted to transmit and receive, said ultrasonic transducer having a substantially concave focusing surface having an active area directed outwardly of said protective sheath member and toward said solution;

c) a reflecting member mounted externally by mechanical support means to said protective sheath member for measurement of high levels of entrained gaseous material spatially separated from said active area of said focusing surface and cooperating therewith so that upon activation of said transducer, ultrasonic waves emitted from said active area pass through said photographic solution, reflect off said reflecting member thereby producing a backscattered signal detectable by said transducer, said backscattered signal having an amplitude inversely proportional to the amount of entrained gaseous material; and, d) a focal zone of the ultrasonic transducer for measurement of low levels of entrained gaseous material, wherein when said ultrasonic waves reflect off said gaseous material in the focal zone a backscattered signal detectable by said transducer, said backscattered signal having an RMS value proportional to the amount of entrained gaseous material is thereby produced.

2. The probe according to claim 1 further comprising means operably connected to said probe for quantifying said backscattered signals and separating said backscattered signals from said reflecting member and said gaseous material, said means comprising a computer.

3. System for measuring entrained gas in a solution, said system comprising:

a) a probe comprising:

a protective sheath member, adapted to be inserted into the solution;

an ultrasonic transducer oriented and encased in said protective sheath member;

said ultrasonic transducer adapted to transmit and receive, said ultrasonic transducer having a substantially concaved focusing element having an active area directed outwardly of said protective sheath member into said solution;

a reflecting member mounted externally by mechanical support means to said protective sheath member for determining high levels of entrained gaseous material spatially separated from said active area of said focusing element and cooperating therewith so that upon activation of said transducer, ultrasonic waves emitted from said active area pass through said solution, reflect off said reflecting member thereby producing a backscattered signal detectable by said transducer, said backscattered signal having an amplitude inversely proportional to the amount of entrained gaseous material; and, a focal zone of the ultrasonic transducer for measurement of low levels of entrained gaseous material, wherein when said ultrasonic waves reflect off said gaseous material in the focal zone a backscattered signal detectable by said transducer that causes an output having an RMS value proportional to the amount of entrained gaseous material is thereby produced;

b) means operably connected to said probe for digitizing said backscattered signals;

c) quantifying means operably connected to said digitizing means for quantifying said digitized backscattered signals; and, d) means for separating said backscattered signals received from said reflecting member and said gaseous material.

4. The system according to claim 3 wherein said reflecting member is mounted perpendicularly to a side mount attached to an end of said protective sheath, and axially of said ultrasonic transducer.

5. The system according to claim 3 wherein said protective sheath member is substantially tubularly shaped.

6. Method of measuring a gaseous material entrained in a photographic solution stream, said method comprises the steps of:

a) providing a probe for measuring gaseous material, said probe having:

a protective sheath member, adapted to be inserted into the solution;

an ultrasonic transducer mounted in said protective sheath member;

said ultrasonic transducer oriented and adapted to transmit and receive, said ultrasonic transducer having a substantially concaved focusing surface having an active area directed outwardly of said protective sheath member into a solution stream;

a reflecting member externally by mechanical support means mounted to said protective sheath member for determining high levels of entrained gaseous material spatially separated from said active area of said focusing element and cooperating therewith so that upon activation of said transducer, ultrasonic waves emitted from said active area pass through said solution, reflect off said reflecting member thereby producing a backscattered signal detectable by said transducer, said backscattered signal having an amplitude inversely proportional to the amount of entrained gaseous material; and, a focal zone of the ultrasonic transducer for measurement of low levels of entrained gaseous material, wherein when said ultrasonic waves reflect off said gaseous material in the focal zone a backscattered signal detectable by said transducer, said backscattered signal having an RMS value proportional to the amount of entrained gaseous material is thereby produced;

b) inserting said probe into said solution;

c) energizing said transducer;

d) receiving backscattered waves from said gaseous material and said reflecting member;

e) converting said received backscattered waves into electrical signals;

f) separating said electrical signals so that gaseous material signals and reflecting member signals are capable of independent processing; and, g) analyzing separated electrical signals.

* * * * *

UNITED STATES PATENT AND TRADEMARK OFFICE
CERTIFICATE OF CORRECTION

PATENT NO.   :   5,454,255
DATED        :   October 3, 1995
INVENTOR(S)  :   Kraus, et al It is certified that error appears in the above-indentified patent and that said Letters Patent is hereby corrected as shown below:

Column 6, Line 1 should read --an ultrasonic transducer encased in said--.

Column 6, Line 3 should read --graphic solution, said ultrasonic transducer oriented and adapted to--.

Column 6, Line 37 should read --an ultrasonic transducer encased in said--.

Column 6, Line 39 should read --said ultrasonic transducer oriented and adapted to transmit and--.

Column 6, Line 60 should read --signal detectable by said transducer said backscattered signal--.

Column 7, Lines 26-27 should read --a reflecting member mounted externally by mechanical support means to said protective sheath member for--.

Signed and Sealed this

Twenty-sixth Day of December, 1995

Attest:

BRUCE LEHMAN

*Attesting Officer*      *Commissioner of Patents and Trademarks*